United States Patent [19]

Staats

[11] Patent Number: 5,531,984

[45] Date of Patent: *Jul. 2, 1996

[54] ANTIMICROBIAL COMPOSITION

[75] Inventor: Victor Staats, Miami Beach, Fla.

[73] Assignee: International Laboratory Technology Corp., Miami Beach, Fla.

[*] Notice: The term of this patent shall not extend beyond the expiration date of Pat. No. 5,417,968.

[21] Appl. No.: 287,206

[22] Filed: Aug. 8, 1994

Related U.S. Application Data

[63] Continuation-in-part of Ser. No. 106,513, Aug. 16, 1993, Pat. No. 5,417,968.

[51] Int. Cl.⁶ ............................ A61K 31/74; A61K 9/70; A01N 25/08; A01N 25/34

[52] U.S. Cl. .................................. 424/78.07; 424/78.02; 424/78.03; 424/78.08; 424/443; 424/409; 424/411; 424/443

[58] Field of Search ........................... 424/78.02, 78.03, 424/78.07, 78.08, 443, 409, 411

[56] References Cited

U.S. PATENT DOCUMENTS 5,232,691  8/1993  Lemole ................................ 424/78.02

*Primary Examiner*—Carlos Azpuru
*Attorney, Agent, or Firm*—Robert M. Downey

[57] ABSTRACT

An antimicrobial composition having antiviral, antibacterial and antifungal properties and including a first quaternary ammonium compound, a second quaternary ammonium compound, a nonionic surfactant and a stabilizer.

4 Claims, No Drawings

ANTIMICROBIAL COMPOSITION

This patent application is a continuation-in-part application of patent application 08/106,513 filed on Aug. 16, 1993, now U.S. Pat. No. 5,417,968.

BACKGROUND OF THE INVENTION

1. Field of the Invention

The present invention relates to an antimicrobial compostion, and more particularly an antiviral, antibacterial and antifungal composition for use alone or in combination with other chemical elements.

SUMMARY OF THE INVENTION

The present invention provides a novel composition having excellent antiviral, antibacterial and antifungal properties to provide a barrier against a broad spectrum of potential pathogens. The composition of the present invention is useful alone as an effective antiviral, antibacterial and antifungal substance to provide a hard surface disinfectant, cold sterilization product, ultrasonic cleaning solution, leather treatment product to prevent growth of fungus, and a disinfectant for swimming pools, hot tubs and other water systems. Additionally, the composition of the present invention can be used in numerous products including, but not limited to, disinfectant hand soaps, hypo-allergenic hand care creme, shampoo, face soap, laundry products, dish washing products (including a bar glass dip) bathroom cleaning products, dental products (e.g., mouthwash, dental adhesive, saliva injector filters, water filtration) and deodorizing products. Further, the composition of the present invention can be used in combination with other chemical elements including hydrophilic compounds and hydrophobic polymers as specifically set forth in previous patent application Ser. No. 106,513, now U.S. Pat. No. 5,417,968, to provide such products as a prophylactic skin barrier providing antiviral, antibacterial and antifungal protection.

The composition of the present invention includes, in combination, a first quaternary ammonium compound, a second quaternary ammonium compound, a nonionic surfactant and a stabilizer.

In accordance with the present invention, it is a primary object to provide an all-purpose antimicrobial composition having excellent antiviral, antibacterial and antifungal characteristics.

It is a further object of the present invention to provide an antimicrobial composition for use individually as an antiviral, antibacterial, antifungal substance.

It is yet a further object of the present invention to provide a composition having antiviral, antibacterial and antifungal characteristics for use in a wide range of products including soaps, cleaning products, disinfectants, cleaning solutions, laundry products, dental products, medical products and the like.

It is still a further object of the present invention to provide a composition having antiviral, antibacterial and antifungal properties and which is specifically structured for use in combination with other chemical elements such as, but not limited to, hydrophilic polymeric components and hydrophobic components such that the composition of the present invention breaks down and precipitates upon contact with moisture, thus activating the composition to provide protection for a predetermined period of time not less than four hours.

These and other objects will become readily apparent from the detailed description which follows.

DETAILED DESCRIPTION OF THE PREFERRED EMBODIMENT

The present invention is directed to an antiviral, antibacterial, antifungal composition for use in a wide range of products. The composition is biologically active against a broad spectrum of viruses, bacteria, fungii, and other pathenogenic species. Specifically, the composition of the present invention has been found to kill virus, bacteria and fungus (including the HIV virus) associated with sexually transmitted diseases. The biologically active composition of the present invention includes a first quaternary ammonium compound, a second quaternary ammonium compound and a nonionic surfactant. The first quaternary ammonium compound is a blend of Myristalkonium chloride and Quaternium 14 shown by the general formula:

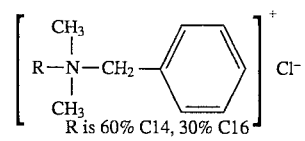

n-alkyl dimethyl benzyl ammonium chloride

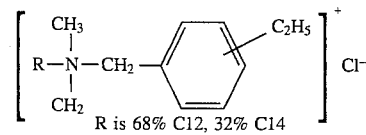

n-alkyl dimethyl ethylbenzyl ammonium chloride

The preferred second quaternary ammonium compound is a mixture of alkylbenzyldimethylammonium chlorides (Benzalkonium Chloride) of the general formula:

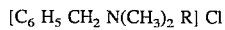

wherein R is alkyl.

Preferably, the nonionic surfactant is Nonoxynol 9 or Triton X-100. Nonoxynol 9 is an ethoxylated nonyl phenol containing 9 moles of ethylene oxide and serves both as a nonionic surfactant and an antimicrobial agent. Triton X-100 is a polyoxyethylene ether which is also a nonionic surfactant and provides antimicrobial properties. Although the surfactant and the quaternary ammonium compounds have biocidal properties and can function to a certain degree alone, a synergistic effect is achieved when they are used in combination, producing substantially greater biocidal activity against pathogenic species. The surfactant enables the composition to be applied evenly over a surface, thus achieving and maintaining a uniform antiviral, antimicrobial and antifungal effectiveness throughout the entire surface. The surfactant further acts as a wetting agent which broadens the effectiveness of the quaternary ammonium compounds. Nonoxynol 9 or triton X-100 is preferably present in the amount of 1%–10% by weight, the first quaternary ammonium compound blend in the amount of 0.02%–1% by weight, and the Benzalkonium Chloride in the amount of 0.1%–0.13% by weight.

In order to stabilize the two quaternary ammonium compounds and surfactant, 1,3 butylene glycol is provided in the composition of the present invention in an amount of between 1%–10% by weight. 1,3 butylene glycol stabilizes the composition and also further adds in the dispersion of the combined quaternary compounds and surfactant to provide a uniform antibacterial, antiviral and antifungal kill rate. The 1,3 butylene glycol further permits other chemical compounds such as hydrophilic agents and hydrophobic polymers to be added to the composition.

Finally, the composition includes deionized water in an amount of between 80%–97.8% by weight of the composition.

The formation of the composition of the present invention requires combining the quaternary ammonium compound blend, the Benzalkonium Chloride, the surfactant, the 1,3 butylene glycol and water in a stainless steel mixing tank and subsequently mixing the combined elements until completely blended to form a homogeneous mixture.

It is contemplated that the resultant composition of the present invention can be used independently of any further combined chemical compounds or elements for use as an effective antiviral, antibacterial and antifungal disinfectant. Alternatively, the composition of the present invention can be incorporated into other products to provide the desired antibacterial, antiviral and antifungal effects. Further, additional compounds or chemical elements can be blended with the composition to achieve a desired result such as forming a prophylactic skin barrier which becomes activated upon contact with moisture.

While this invention has been shown and described in a preferred embodiment, it is recognized that departures may be made within the spirit and scope of the invention which should not, therefore, be limited except by the following claims and within the doctrine of equivalents.

Now that the invention has been described,

What is claimed is:

1. A composition comprising:

a first quaternary ammonium compound including a blend of n-alkyl dimethyl benzyl ammonium chloride and n-alkyl dimethyl ethylbenzyl ammonium chloride in an amount of between 0.02%–1.0% by weight of said composition, a second quaternary ammonium compound in an amount of between 0.1%–0.13% by weight of said composition, a nonionic surfactant in an amount of between 1%–10% by weight of said composition, 1,3 butylene glycol in an amount of between 1%–10% by weight of said composition, and deionized water in an amount of between 80%–97.8% by weight of said composition.

2. The composition as recited in claim 1 wherein said second quaternary ammonium compound is a mixture of alkylbenzyldimethylammonium chlorides.

3. The composition as recited in claim 1 wherein said surfactant is an ethoxylated nonyl phenol containing 9 moles of ethylene oxide.

4. The composition as recited in claim 1 wherein said surfactant is polyoxyethylene ether.

* * * * *